(12) United States Patent
Bibian et al.

(10) Patent No.: US 11,337,633 B1
(45) Date of Patent: *May 24, 2022

(54) METHOD AND SYSTEM FOR ELECTRODE IMPEDANCE MEASUREMENT

(71) Applicants: Stephane Bibian, Cleveland Heights, OH (US); Tatjana Zikov, Cleveland Heights, OH (US)

(72) Inventors: Stephane Bibian, Cleveland Heights, OH (US); Tatjana Zikov, Cleveland Heights, OH (US)

(73) Assignee: NeuroWave Systems Inc., Cleveland, OH (US)

(*) Notice: Subject to any disclaimer, the term of this patent is extended or adjusted under 35 U.S.C. 154(b) by 805 days.

This patent is subject to a terminal disclaimer.

(21) Appl. No.: 15/966,039

(22) Filed: Apr. 30, 2018

Related U.S. Application Data

(63) Continuation of application No. 13/110,455, filed on May 18, 2011, now Pat. No. 9,980,662.

(Continued)

(51) Int. Cl.
*A61B 5/291* (2021.01)
*A61B 5/00* (2006.01)
*A61B 5/053* (2021.01)

(52) U.S. Cl.
CPC .............. *A61B 5/291* (2021.01); *A61B 5/053* (2013.01); *A61B 5/7203* (2013.01);
(Continued)

(58) Field of Classification Search
None
See application file for complete search history.

(56) References Cited

U.S. PATENT DOCUMENTS 3,230,950 A * 1/1966 Buffington ............. A61B 5/022
600/493
3,623,477 A * 11/1971 Trent ................... A61B 5/0478
600/383

(Continued)

OTHER PUBLICATIONS

Voss, L., & Sleigh, J. (2007). Monitoring consciousness: The current status of Eeg-based depth of Anaesthesia Monitors. Best Practice & Research Clinical Anaesthesiology, 21(3), 313-325. doi:10.1016/j.bpa.2007.04.003 (Year: 2007).*

*Primary Examiner* — Jason M Sims
*Assistant Examiner* — James Stewart Stambaugh, III
(74) *Attorney, Agent, or Firm* — Brian Kolkowski

(57) ABSTRACT

The present invention relates to measuring electrical impedance, and particularly to measuring impedance of electrodes used to acquire physiological signals. The measurement of electrode impedance is typically performed to ensure proper electrode-to-skin contact, and thus verify the quality of the acquired signals. Electrode-to-skin contact impedance has also clinical utility for monitoring, diagnosis, prognosis or treatment, as it can be used to measure skin conductivity, which is function of physiological processes. The present invention relates in particular to a substantially continuous method for performing such measurement. The measurement is performed in such a way that it does not affect the bioband, the range (or ranges) of frequencies that contains components used for diagnostic, prognostic, triage, and/or treatment purposes. The present invention therefore performs this impedance measurement without affecting the physiological signal while allowing for uninterrupted monitoring of said signal.

18 Claims, 8 Drawing Sheets

Related U.S. Application Data

(60) Provisional application No. 61/348,134, filed on May 25, 2010.

(52) U.S. Cl.
CPC .......... *A61B 5/7221* (2013.01); *A61B 5/4094* (2013.01); *A61B 5/4806* (2013.01); *A61B 5/4821* (2013.01); *H05K 999/99* (2013.01)

(56) References Cited

U.S. PATENT DOCUMENTS

| | | | | |
|---|---|---|---|---|
| 3,807,387 A * | 4/1974 | MacNichol, Jr. | A61B 5/0476 | 600/544 |
| 3,882,277 A * | 5/1975 | DePedro | A61B 5/0006 | 379/106.02 |
| 4,092,981 A * | 6/1978 | Ertl | A61B 5/04014 | 600/544 |
| 4,307,726 A * | 12/1981 | Paulson | A61B 5/05 | 600/407 |
| 4,308,873 A * | 1/1982 | Maynard | A61B 5/04004 | 600/378 |
| 4,564,022 A * | 1/1986 | Rosenfeld | A61B 5/0484 | 600/544 |
| 4,579,125 A * | 4/1986 | Strobl | A61B 5/742 | 600/544 |
| 4,753,246 A * | 6/1988 | Freeman | A61B 5/048 | 600/544 |
| 4,800,893 A * | 1/1989 | Ross | A61B 5/0482 | 600/545 |
| 4,928,704 A * | 5/1990 | Hardt | A61B 5/0482 | 600/545 |
| 5,325,862 A * | 7/1994 | Lewis | A61B 5/1171 | 600/544 |
| 5,795,293 A * | 8/1998 | Carim | A61B 5/04025 | 600/372 |
| 5,859,527 A * | 1/1999 | Cook | H02M 7/103 | 323/298 |
| 6,032,060 A * | 2/2000 | Carim | A61N 1/0472 | 600/372 |
| 6,366,813 B1 * | 4/2002 | DiLorenzo | A61B 5/048 | 607/45 |
| 9,980,662 B2 * | 5/2018 | Bibian | A61B 5/0478 | |
| 2002/0183634 A1 * | 12/2002 | Rantala | A61B 5/0488 | 600/509 |
| 2004/0039418 A1 * | 2/2004 | Elstrom | A61B 5/04 | 607/3 |
| 2004/0138516 A1 * | 7/2004 | Osorio | A61N 1/36132 | 600/9 |
| 2006/0020218 A1 * | 1/2006 | Freeman | A61B 5/0424 | 600/509 |

* cited by examiner

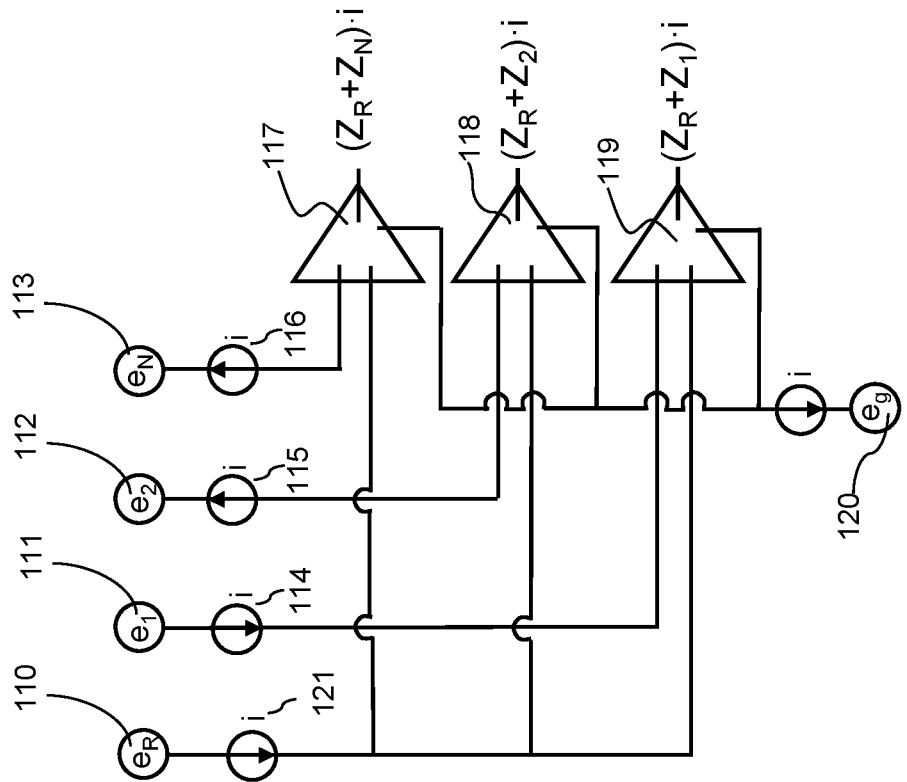
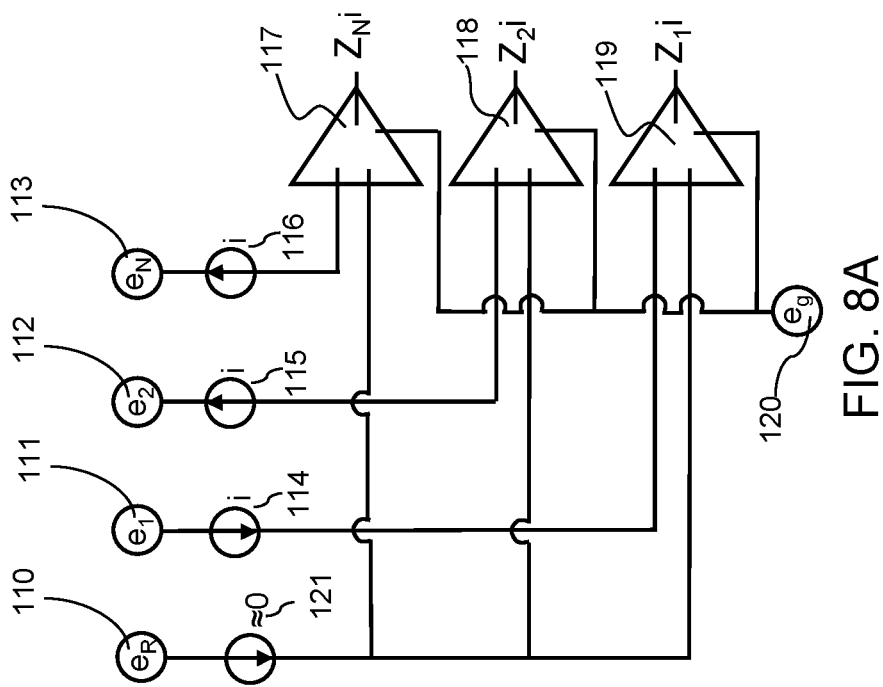
FIG. 8B
FIG. 8A

METHOD AND SYSTEM FOR ELECTRODE IMPEDANCE MEASUREMENT

CROSS-REFERENCE TO RELATED APPLICATIONS

This application claims priority to U.S. Provisional Application, Ser. No. 61/348,134, which was filed on May 25, 2010.

BACKGROUND OF THE INVENTION

1. Field of the Invention

The present invention relates to measuring electrical impedance, and particularly electrode impedance used to acquire physiological signals. The measurement of electrode impedance is typically performed to ensure proper electrode-to-skin contact, and thus verify the quality of the acquired signals. It can also be used to determine skin conductivity, which is a function of physiological processes such as sweating, and can be used to determine the level of autonomic activation as a result of psychological or physiological stress.

The present invention relates in particular to a continuous method for performing such measurement. The measurement is performed in such a way that it does not affect the bioband of the signal. In this application, we define the bioband as the range (or ranges) of frequencies that contains components used for diagnostic, prognostic, triage, and/or treatment purposes. The method and system disclosed herein further provides the means to perform the measure of the impedance of each single electrode. Finally, this measurement can be done either at one particular frequency (including 0 Hz), or at different frequencies simultaneously.

2. Technology Review

Virtually all forms of biomedical/physiological signal monitoring rely on physiological sensors to provide as clear and accurate of a signal as possible. The most commonly used form of these sensors is electrodes, particularly physiological electrodes. Common examples of such physiological signal monitoring techniques include electroencephalography (EEG), electrocardiography (EKG), electromyography (EMG), and electrooculography (EOG), although this list is not exhaustive. Each of these signal monitoring techniques utilizes the placement of physiological electrodes to conduct the corresponding signals to the signal processing hardware. However, the quality of physiological signals, and therefore the accuracy and usefulness of the subsequent signal processing, is subject to the quality of the connection between the electrode and the subject or patient's body, the quality of the connection between the monitoring device and electrode as well as the fidelity of the electrode itself.

Poor physiological signal quality can result in high impedance which in turn decreases the quality or strength of the signal received. High impedance detrimentally affects physiological signal quality by potentially making it more difficult to distinguish a weaker physiological signal from artifacts or other noise in the system. If impedance is particularly high, the signal may not even be conducted through the electrode and therefore may not reach the monitoring equipment at all.

Additionally, artifacts may be created if signal quality decreases and impedance rises. One example is if an electrode moves from its position on the subject or patient's skin and therefore the signal is transmitted intermittently. Not only is impedance increased, perhaps on an intermittent basis, as a result of the break in connection between the electrode and the subject or patient's skin, but the movement of the electrode may create artifacts in the signal when it is properly recorded. Although there are signal processing techniques to remove or correct artifacts, it is of course better to minimize the occurrence of such artifacts.

These issues can potentially lead to inaccurate analysis, which in turn can create potentially serious problems such as incorrect or missed diagnoses of illness, or other physiological manifestations. Ensuring fidelity of signal quality starting with the electrodes conducting these physiological signals is an important issue. Measuring impedance to maintain good signal quality, however, generally interrupts the signal monitoring process. Supplying an electrical current to an electrode to measure impedance typically causes an artifact, spike or perturbation in the monitored physiological signal. Not only does that perturbation interfere with the signal itself, but it causes the data at various points of time surrounding it to become corrupted. Usually, the perturbation and the portions of the signal affected by it must be removed from the signal and therefore gaps are created in the data being collected. When there are gaps in the data there may be significant or important physiological activity that may be missed lead to incorrect or missed diagnoses, improper treatment, and the like.

Perturbation is generally caused by supplying or removing a current for measuring impedance to the electrodes substantially instantaneously; that is, the current is supplied, in effect, at full load. In other words, the current resembles a square wave where the current increases to full load when it is turned on and to no load when it is turned off. When supplying the current this way to check for impedance problems, the electrical pulse disrupts, or perturbs, the electrical EEG signal being monitored, and as it is proportionally much larger or stronger than the physiological EEG signal, and that physiological signal is lost within the artifact created by the electrical pulse. A period of time is necessary for the signal to recover from the perturbation as the oscillations lose power over time. This time period is the gap where data is lost.

It is therefore an object of the present invention to provide a system and method that meets all of these needs and others where such a device and method would be applicable. It is another object of the present invention that this system and method be capable of checking electrical impedance in physiological electrodes both manually on demand as well as in an automated fashion, and both in a substantially continuous manner. It is also an object of the present invention that that this system and method minimize data loss from impedance measurement. Finally, it is an object of the present invention that physiological signals are transmitted correctly and efficiently to increase the accuracy and fidelity of the signal processing methods and ensure accurate diagnosis and treatment.

SUMMARY OF THE INVENTION

The present invention relates to a physiological monitor and system, more particularly to an electroencephalogram (EEG) monitor and system, even more particularly to an EEG monitor and system capable of substantially continuously measuring electrical impedance in electrodes for the purpose of measuring signal quality while at the same time minimizing data loss due to perturbation of the physiological signal.

Electrode impedance measurement methods are a necessary tool for all physiological monitoring and measurement techniques. Impedance measurement methods ensure that the physiological signal is transmitted as accurately and as clearly as possible from the subject or patient to the monitoring system and equipment. However, it is equally important to obtain as much usable data as possible during the monitoring time period, and current impedance measurement methods can create gaps in the data collected as a result of perturbations in the physiological signal due to the electrical current used to measure impedance. Continuous impedance measurement provides reliable signal monitoring over the entirety of the measurement period.

In order to avoid this perturbation in the EEG signal, the present invention supplies and/or removes an electrical current (used to test and measure electrical impedance of the electrode) progressively, as opposed to substantially instantaneously. By progressively supplying or removing the electrical current for impedance measurement, a perturbation or pulse effect is eliminated. The perturbation, spike, or pulse effect interferes with the EEG signal, which is much weaker than the test and measurement signal used to determine impedance levels. Eliminating the spike or pulse effect therefore eliminates the perturbation of the physiological signal and all that is recorded is that EEG signal. No data is lost because the EEG signal is monitored and recorded continuously without interruption or corruption by the addition or removal of the electrical current used to measure electrode impedance.

These methods are designed particularly for use with electroencephalography (EEG) signals, but can also be used with other physiological signals, including electrocardiography (ECG), electrical impedance tomography (EIT), electromyography (EMG) and electro-oculography (EOG), and the like. These methods and the systems and devices using these methods preferably can be used for brain dysfunction or activity monitoring such as for anesthesia monitoring, for seizure detection, for sedation monitoring and the like. These methods and the systems and devices using these methods preferably can be used with equipment for the operating room, acute care such as the intensive care unit, critical care such as the emergency room or in the field. These methods and the systems and devices using these methods can be used by anesthesiologists, nurse anesthetists, neurologists and neurosurgeons, pulmonologists, emergency room physicians and clinicians, intensive care physicians and clinicians, medics, paramedics, emergency medical technicians, respiratory technicians, and the like. Preferably, these methods and the systems and devices using these methods can be used by individuals or clinicians with little or no training in signal analysis or processing. These methods preferably are used with anesthesia monitors, seizure detectors, sedation monitors, sleep diagnostic monitors, any sort of ECG monitor, any sort of EEG monitor, battlefield monitors, operating room monitor, ICU monitor, emergency room monitor, and the like.

Preferably, the system or monitor is constructed to be rugged, so as to withstand transport, handling and use in all of the applications listed above including in emergency scenarios, such as on the battlefield or in mass casualty situations, or to reliably survive daily use by emergency medical personnel or other first responders. The system or monitor should preferably be splash-proof (or water tight), dust-tight, scratch-resistant, and resistant to mechanical shock and vibration. The system or monitor should preferably be portable and field-deployable in particular embodiments to a military theater of operation, the scene of an accident, the home of a patient, or to any clinical setting.

The system or monitor should preferably be designed for non-expert use. By this, it is meant that a person should not be required to possess extraordinary or special medical training in order to use the system effectively and reliably. The system should therefore preferably be automatic in operation in a number of respects. First, the system should be capable of automatic calibration. Second, the system should preferably have automatic detection of input signal quality; for example, the system should be capable of detecting an imbalance in electrode impedance. Third, the system should preferably be capable of artifact detection and removal on one or more levels, so as to isolate for analysis that part of the signal which conveys meaningful information related to a subject or patient's cortical activity, level of consciousness, occurrence of a seizure, level of sedation and the like. Fourth, the system should preferably include outputs which result in visual and/or audible feedback capable of informing the user of the state of the subject or patient related to quantification of signal quality, cortical activity, level of consciousness, occurrence of a seizure, level of sedation and the like at any time during the period of time that the system was monitoring the subject or patient.

Preferably, the system should operate in real time. One example of real-time operation is the ability of the system to detect increased electrical impedance in an electrode as it rises, rather than detecting it after it has risen and substantially affected signal quality and therefore data acquisition for any period of time.

Also preferably, the system should operate substantially continuously. One example of substantially continuous impedance measurement is the ability of the system to measure the electrical impedance of at least one electrode at all time periods or points, except for the time period(s) during which the electrical current is being supplied to the electrodes is increased or decreased. Preferably, the current is supplied progressively until it reaches preferably a stabilized, maximum predetermined level, at which time the system immediately begins measuring impedance of at least one electrode until the current is progressively decreased to a minimum value (preferably zero), which also preferably is stabilized.

The system described in this invention also preferably incorporates a number of unique features that improve safety, performance, durability, and reliability. The system should be cardiac defibrillator proof, meaning that its electrical components are capable of withstanding the surge of electrical current associated with the application of a to cardiac defibrillator shock to a subject or patient being monitored by the system, and that the system remains operable after sustaining such a surge. The system should have shielded leads so as to reduce as much as possible the effects of external electromagnetic interference on the collection of biopotential or physiological signals from the subject or patient being monitored by the system. The system should be auto-calibrating, more preferably capable of compensating for the potential differences in the gains of the input channels to the subject or patient module. The system should be capable of performing a continuous impedance check on its electrode leads to ensure the suitability of monitored signals.

One embodiment of the present invention involves a device for the measurement of electrical impedance in electrodes comprising at least three electrodes attached to a subject, at least one electrode being for electrical grounding, at least one electrode providing a reference signal, and at least one measurement electrode for acquisition of a physiological signal, a processor for collection of the physiological signal and determining the electrical impedance of each electrode, a variable current source capable of progressively increasing and decreasing electrical current into the individual electrodes, and a monitor to display the physiological signal and calculated electrical impedance for each electrode utilized.

Another embodiment of the present invention is a method of measuring electrical impedance of electrodes from an EEG acquisition device comprising steps of acquiring an EEG signal from a subject or patient with an EEG acquisition device during an EEG measurement period, utilizing at least three separate electrodes with the acquisition device, at least two electrodes being a first measurement and a second measurement electrode, used for actual EEG measurements, and one electrode for electrical grounding, supplying a first electrical current to the first measurement electrode at a defined frequency, calculating a first electrode electrical impedance value from the first measurement electrode by measuring a voltage across the first and second measurement electrodes, supplying a progressively increasing second electrical current to the second measurement electrode at the defined frequency, calculating a second electrode electrical impedance value by measuring a voltage across the first and second measurement electrodes to determine a total impedance for the first and second measurement electrodes and subtracting the first electrode electrical impedance value, progressively decreasing the second electrical current from the second electrode to remove the electrical current, and repeating the above steps substantially continuously during the subject or patient measurement period.

Yet another embodiment of the present invention is a method of measuring electrical impedance of electrodes comprising steps of acquiring an EEG signal from a subject or patient with an EEG acquisition device during an EEG measurement period, utilizing at least three separate electrodes, at least two electrodes being a first measurement and a second measurement electrode, used for actual EEG measurements, and one electrode for electrical grounding, supplying a first electrical current to the first measurement electrode at a defined frequency, calculating a first electrode electrical impedance value in the first measurement electrode by measuring a first voltage across all the measurement electrodes, supplying a progressively increasing second electrical current to the second measurement electrode while essentially simultaneously progressively decreasing the first electrical current provided to the first measurement electrode, calculating a second electrical impedance value of the second measurement electrode by measuring a voltage across all the measurement electrodes, providing a progressively increasing first electrical current to the first measurement electrode while essentially simultaneously progressively decreasing the second electrical current provided to the second measurement electrode, and repeating the above steps substantially continuously during the subject or patient measurement period.

Still other embodiments of the present invention include using these methods in conjunction with acquiring an ECG, EOG, EMG, and/or EIT signal from a subject or patient with a corresponding acquisition device during a subject or patient measurement period.

Still another embodiment of the present invention is a method of progressively supplying and/or removing electrical currents to/from electrodes comprising steps of increasing the level of the electrical current provided to an electrode over a period of time not less than 0.25 seconds from a value of zero nA (nanoamperes) to a maximum predetermined level, where the current preferably does not increase at a rate high enough to cause perturbation in the physiological signal, holding the electrical current at the predetermined frequency and at the maximum predetermined level during a period of time of at least one cycle of the measurement current while a voltage is measured and electrode impedance is calculated, and decreasing the level of the electrical current provided to the electrode over a period of time not less than 0.25 seconds from the maximum predetermined level to zero nA where the current preferably does not decrease at a rate high enough to cause perturbation in the physiological signal. An example of a rate of increase in the impedance measurement current that would create very little perturbation and would therefore be acceptable would be to increase the current around a rate of 20 nA per second, over a time period not less than 0.25 seconds.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

BRIEF DESCRIPTION OF THE DRAWINGS

FIGS. 8 A-B. Diagram depicting another example of a multiple lead referential system of measurement of electrical impedance in physiological electrodes.

DETAILED DESCRIPTION OF THE DRAWINGS

Figure 1:
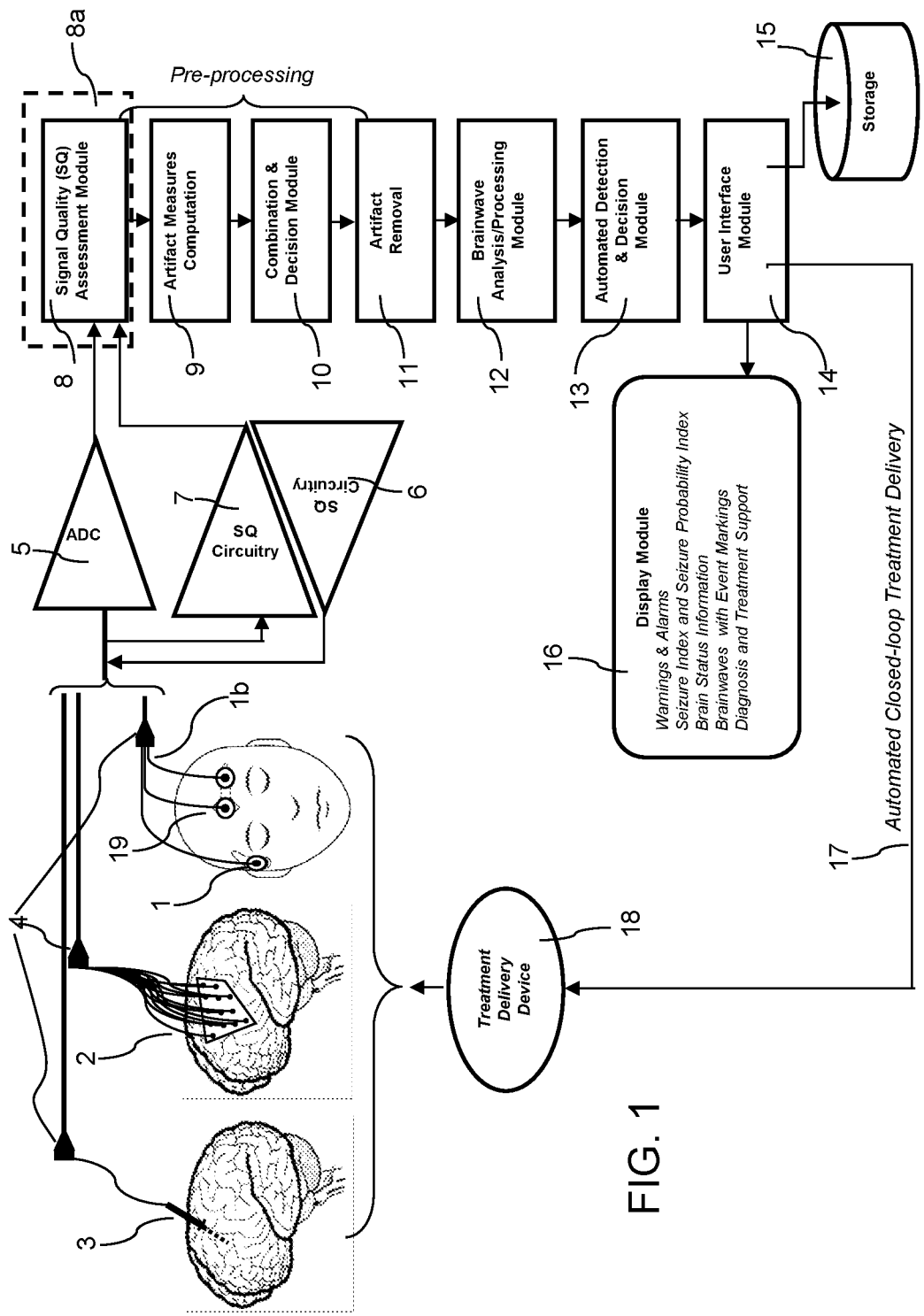
FIG. 1. Block diagram of a system overview for real-time applications.

The present invention relates to a physiological monitor and system, more particularly to an electroencephalogram (EEG) monitor and system, and a method of detecting the presence or absence of artifacts and possibly removing artifacts from an EEG or other signal without corrupting or compromising the signal.

Various embodiments of the present invention include one or more of the following components, and variations thereof. These components include but are not limited to electrodes for attaching to the subject or patient, a processor for the collection of the electrode signal, a variable current source which is capable of progressively supplying and/or reducing the electrical current, and a device for at a minimum alerting the user of poor impedance or monitoring impedance. These components can be used alone or with other systems incorporating these types of components where impedance of an electrode is important in the function of the device or system.

The present invention is designed for use with physiological signals collected with conductive type electrodes. The methods, devices and systems using those devices of the present invention should be able to work with any type of physiological signals and their corresponding electrodes, including but not limited to electroencephalography (EEG), electrooculography (EOG), electromyography (EMG), electrocardiography (ECG), electrical impedance tomography (EIT), and the like. The electrodes used with this device or system can be those types currently available, or that may become available for use with physiological signals in the future. Typically, to maintain good signal quality, electrodes may be applied with conductive paste or gel to create a to connection between the subject or patient and the electrode. This paste or gel serves to reduce the impedance in the electrode. Alternatively, the subject(s) skin may be mechanically abraded, the electrode may be amplified or a dry electrode may be used. Dry physiological recording electrodes of the type described in U.S. Pat. No. 6,785,569 can be used. U.S. Pat. No. 6,785,569 is hereby incorporated by reference. Dry electrodes provide the advantage that there is no gel to dry out, no skin to abrade or clean, and that the electrode can be applied in hairy areas such as the scalp.

Preferably the device for and methods of measuring impedance of the electrodes is used with electrodes. The electrodes of the present invention can be individual electrodes or an array. These individual electrodes, or an array of electrodes is attached to a subject or patient. Preferably at least two electrodes are used. More preferably at least three electrodes are used. Still more preferably at least four electrodes are used. Even more preferably at least five electrodes are used. More preferably still at least six electrodes are used. Even still more preferably at least seven electrodes are used. Most preferably eight electrodes or more are attached to the patient or subject.

Of the electrodes used, preferably at least one electrode should be for electrical grounding. Electrical grounding protects the subject or patient from surges in electrical power. Additionally, grounding serves to protect the monitoring equipment, particularly amplifiers, from surges of electrical power as well as from the build up of static electricity and the like which could damage the equipment and decrease its ability to perform its monitoring function accurately and safely. The grounding electrode redirects any excess electrical charge through a safe outlet where it will not harm the subject or patient, or the equipment. Grounding also allows for the use of differential amplifiers, which further allows for the rejection of common-mode noise (i.e., noise common to the two measurement electrodes).

Additionally, at least one electrode should provide a reference EEG signal. Typically, EEG signals are representative of the differences in voltage between two electrodes, and therefore it is common to designate a reference electrode which is used to compare against the measurement electrodes. The reference electrode(s) can be placed anywhere on the subject's or patient's scalp for EEG signal recording, however, preferably the electrode is placed near the center of the subject's or patient's head (i.e. near the longitudinal fissure of the brain) in order to avoid amplifying the activity of one brain hemisphere over the other. Another common location for reference electrodes is at the subject's or patient's ear(s), depending on the type of electrode montage used. The reference electrode provides an outlet for an injected electrical current and gives a basis of measurement. Preferably, the reference electrode is used in conjunction with each of the measurement electrodes to measure voltage differences between those measurement electrodes and the reference electrode. This provides a constant which allows for the signals of the measurement electrodes to be isolated and compared.

Optionally a measurement electrode can be used as a reference for another measurement electrode. One example, a "bipolar montage," is a method where two adjacent electrodes are compared against each other. In this method, the electrodes used are generally at least two measurement electrodes, and no separate reference electrode is necessary because one measurement electrode being used as a reference at given times. Another example is the "average reference montage" where the signals from each of the measurement electrodes are summed and averaged, and that average signal is used as the reference signal against which the individual measurement signals are compared. Yet another example is "Laplacian montage" in which each EEG channel represents the difference between the given measurement electrode signal and a weighted average of the surrounding measurement electrode signals.

Also, at least one measurement electrode should be a measurement electrode for acquisition of the EEG signal from the subject's or patient's brain. The measurement electrode(s) are generally placed in one of the common locations for brain activity measurement (e.g. frontal (F), parietal (P), anterior (A), central (C) and occipital (O)). As the measurement electrode acquires and transmits the EEG signal from the given portion of the subject's or patient's brain, that signal is compared against the signal from the reference electrode to produce the displayed EEG waveform for that measurement channel. More specifically, the measured voltages for each of the EEG signals from the measurement electrode(s) and the reference electrode(s) are compared to produce the individual EEG channel for each measurement electrode.

Another component of various embodiments of the present invention is a processor for the collection of the EEG signal and for measuring the voltages across combinations of electrodes to determine impedance. A current is supplied to an electrode at a known frequency and amplitude, and travels through the subject's or patient's body. The current subsequently is measured from the subject or patient through the reference or other measurement electrode. The reference or other measurement electrode closes the circuit and allows the electrical current supplied to the first measurement electrode a path to exit the subject's or patient's body. This also creates a voltage across the measurement electrode and the reference electrode which can be measured by the system. The known current and measured voltage values are used to calculate the impedance of the electrode(s). This process is described in greater detail below.

Yet another component of one embodiment of the present invention is a variable current source that is capable of progressively increasing and decreasing electrical current into the individual measurement electrodes. Various electrical components can be used to modulate the electrical current waveform as necessary, including, but not limited to microprocessors, digital to analog converters, modulators, transistors, and the like.

Various embodiments of the present invention supply a current to the measurement electrodes to be used for impedance measurement. Preferably, the current supplied to the measurement electrodes is supplied at a known amplitude and frequency. Also preferably, the frequency of the supplied current is outside of the biological frequency of the physiological signal being monitored (herein referred to as the bio-band). Supplying the current outside the biological frequency for the signal from the electrode being measured prevents interference with the diagnostic signal—preventing perturbation of the measured physiological signal. For example, the typical biological frequency (bio-band) of EEG signals is from about 0.5 Hz to about 70 Hz, but can expand to between 0.125 Hz to about 120 Hz. Meanwhile, the typical bio-band for EMG signals ranges from about 30 Hz up into the kHz range.

Preferably, the electrical current for impedance measurement is supplied at a frequency at least 10% greater than the maximum frequency of the bio-band or at least 10% less than the lower limit of the bio-band. More preferably, the electrical current is supplied at a frequency at least 20% greater than the maximum frequency of the bio-band or at least 20% less than the lower limit of the bio-band. Yet more preferably, the electrical current is supplied at a frequency at least 30% greater than the maximum frequency of the bio-band or at least 30% less than the lower limit of the bio-band. Still more preferably, the electrical current is supplied at a frequency at least 40% greater than the maximum frequency of the bio-band or at least 40% less than the lower limit of the bio-band. Even more preferably, the electrical current is supplied at a frequency at least 50% greater than the maximum frequency of the bio-band or at least 50% less than the lower limit of the bio-band.

It is possible to supply an electrical current for impedance measurement containing various types of frequencies including frequencies within the bio-band. Generally, frequencies within the range of 48 Hz to 62 Hz are filtered out of the physiological signal because of the large amount of noise that is present due to interference from other electrical devices and components as well as the electrical main lines of the buildings. The frequencies filtered out depend on the location. In the United States, generally, electrical power is delivered in the range of 58 to 62 Hz, whereas in Europe it is supplied between 48 and 52 Hz. Clearly, those ranges are both within the bio-band range for EEG signals (i.e. 0 to 120 Hz). It is therefore a possibility to supply the impedance measurement current at a frequency close to that range and to not further adversely affect the resulting electrode signal because the filtering methods quite often are set up to ignore those frequencies where interference results from electrical devices being used about the measurement area. If the device is to be used in the United States, then the impedance measurement current can be supplied at a frequency between 58-62 Hz; if the device is to be used in Europe, then the current can be supplied at a frequency between 48 and 52 Hz; and if the devices needs to be capable of working in both locations then the current can be supplied at a frequency between 48-62 Hz and more preferably about 55 Hz. In all cases, when supplying the impedance measurement current within the bio-band of a physiological signal, the current is preferably supplied as a purely sine wave, or as close to a pure sine wave as possible, to avoid further perturbation of the physiological signal.

Other options allow for a single device to be used in either location, regardless of the frequency of main electrical lines and ambient interference. One such option is to supply the electrical current for impedance testing between the two main electrical frequency bands. This would allow the system to perform impedance tests in either location. With this method, the electrical current would not be completely lost in the noise of main electrical power in either the United States or Europe, but would still be filtered out with the rest of the noise created by those electrical mains and other surrounding electrical interference. Additionally, the system can be designed for use either in the U.S. or Europe by choosing a current frequency to use that fits either scheme, or the system could be designed to detect which location it is in and alter the frequency of the supplied current accordingly.

The current preferably, when supplied is supplied by progressively increasing and decreasing the current. By progressively increasing or decreasing the current, it is meant that the current is increased or decreased from its minimum or maximum respectively, preferably from its minimum (preferably zero) to its maximum level over a period of time or from its maximum to its minimum value (preferably zero) over a period of time also respectively. Preferably, the current is increased or decreased over a period of time not less than 0.25 second. More preferably, the current is increased or decreased over a period of time not less than 0.5 second. Still more preferably, the current is increased or decreased over a period of time not less than 0.75 second. Yet more preferably, the current is increased or decreased over a period of time not less than 1 second. Still more preferably, the current is increased or decreased over a period of time not less than 2 seconds. Even more preferably, the current is increased or decreased over a period of time not less than 3 seconds. More preferably still, the current is increased or decreased over a period of time not less than 5 seconds. Even still more preferably, the current is increased or decreased over a period of time not less than 7 seconds.

Another way to frame the progressive supply of the current is that preferably the current is increased or decreased over a time period between 0.25 second and 5 minutes. More preferably the current is increased or decreased over a time period between 0.5 second and 2. Still more preferably, the current is increased or decreased over a time period between 0.75 second and 1 minute. Yet more preferably, the current is increased or decreased over a time period between 1 second and 30 seconds. Still yet more preferably, the current is increased or decreased over a period of time of between 3 and 20 seconds.

Preferably, the maximum level of the impedance measurement current supplied is less than 10 µA. More preferably, the maximum level of the impedance measurement current supplied is less than 5 µA. Still more preferably, the maximum level of the impedance measurement current supplied is less than 1 µA. More preferably yet, the maximum level of the impedance measurement current supplied is less than 500 nA. Even more preferably, the maximum level of the impedance measurement current supplied is less than 100 nA. More preferably still, the maximum level of the impedance measurement current supplied is less than 50 nA. Even still more preferably, the maximum level of the impedance measurement current supplied is less than 25 nA. Most preferably, the maximum level of the impedance measurement current supplied is less than 12 nA.

The maximum level of the impedance measurement current supplied further depends on the electrical instrumentation utilized as well as legal limits set with regard to patient care, depending on the application. The supplied current must be within the limits of the instrumentation so as not to overload the amplifiers and cause the system to fail. Also, regulations limit currents supplied to the human body to levels below 10 μA.

Still another component of various embodiments of the present invention is a monitor to display the physiological signal and the calculated electrical impedance for each electrode. The monitor can be of any type of visual display monitor capable of showing various electrode signals as well as other information such as the measured impedance of the electrodes used, and like. The monitor can also have other functions. If the electrode impedance device is part of a larger system, then the monitor can be used in that system to display other information. One example is a system for measuring cortical activity of the brain or the affect of anesthetics on the level of consciousness of the subject or patient. With such a system the monitor would also be used to display an index of the cortical activity of the brain or the depth of consciousness. Another example would be a seizure detection monitor. Preferably the monitor is thin and light weight for ease of use and transportation. Also preferably, the monitor is rugged and capable of withstanding significant forces without breaking. This device may also alert the user of the impedance of the electrode(s) through lights, audible warnings, and messages including voice, e-mail, text and the like. Other variations of the device and systems using the device will become evident and are part of this invention.

Various embodiments of the methods of the present invention include one or more of the following steps, and variations thereof. These steps include acquiring an EEG signal from a subject or patient with an EEG acquisition device during an EEG measurement period. In order to acquire an EEG signal from a subject or patient, the electrodes must first be attached. This can be done as described above, utilizing electrodes with conductive paste or gel, mechanically abrading the subject or patient's skin, using dry physiological electrodes, or any combination of these methods. Additionally as described above, the electrodes can be placed at any location on the subject's or patient's head as long as one electrode is attached for electrical grounding, one is placed in a position to acquire a reference signal, and at least one is placed in a position to acquire a measurement signal from some portion of the brain (e.g. frontal (F), parietal (P), anterior (A), central (C) and occipital (O)).

One step includes utilizing at least three separate electrodes with the acquisition device, at least two electrodes being a first measurement and a second measurement electrode, used for actual measurements, and one electrode for electrical grounding.

Another step includes supplying a first electrical current to the first measurement electrode at a defined frequency. This step involves increasing the electrical current supplied to a given electrode from a value of about zero (0) μA to a predefined maximum, at a predefined frequency. If this current is supplied prior to a testing or monitoring time period, then the current can be supplied to this first electrode at any rate. If the system is actively monitoring and recording an signal from the subject, then the current must be supplied progressively, over a period of time.

Another step is calculating a first electrode electrical impedance value from the first measurement electrode by measuring a voltage across the first and second measurement electrodes. When the electrical current is supplied in the previous step, it is applied at a known frequency and amplitude. The system then measures the voltage that results from that electrical current across the two measurement electrodes. Impedance is the complex form of electrical resistance, that is, impedance is the electrical resistance to sinusoidal alternating current (AC). Impedance values take on a complex form containing both a magnitude as well as a phase, which indicates the lag between the current and voltage. Impedance can be calculated as a function of both the magnitudes and the phases of the voltage, current, and impedance in two steps. In various embodiments of the present invention, the first step is very similar to traditional Ohm's law and calculates impedance by dividing the measured voltage by the known current. The phase component describes the fraction of the lagging wave that has been completed by the when it reaches the same reference point as the first signal, in the present case that reference point is the electrode Another step includes supplying a progressively increasing second electrical current to the second measurement electrode at the defined frequency. This step involves increasing the electrical current supplied to a given electrode from a value of about zero (0) μA to a predefined maximum over a period of time in a progressive manner as described above. The electrical current is supplied to this first measurement electrode in order to calculate the impedance value of that electrode and check for signal quality of that electrode. The current must be supplied progressively, over a period of time, so as not to perturb or cause artifacts in the EEG (or other physiological signal) that is being recorded and monitored. Once the current reaches the predetermined maximum value, the system is able to take the required measurements and calculate the impedance of that electrode.

Another step includes calculating a second electrode electrical impedance value by measuring a voltage across the first and second measurement electrodes to determine a total impedance for the first and second measurement electrodes and subtracting the first electrode electrical impedance value. Since the electrical impedance value of the first measurement electrode was already calculated above, it is a known value. This step calculates the total impedance across both measurement electrodes in much the same manner as described above, but provides a total impedance for both electrodes being measured. Once this total impedance value is known, the impedance value of the first measurement electrode is subtracted which leaves the value of impedance only for the second measurement electrode.

Other embodiments of the present invention may involve the essentially simultaneous supplying of an electrical current to a second measurement electrode and reduction of the electrical current to the first measurement electrode. As opposed to the step described above where a current is supplied to more than one measurement electrode and the impedance is calculated by subtracting one electrode's impedance from a total impedance of the electrodes, this step only supplies a current to one electrode at a time and thereby calculates the impedances of each electrode individually. This step provides that the system reduce the current in the first measurement electrode from its maximum value down to about zero (0) µA while also increasing the electrical current supplied to the second measurement electrode from zero to the same maximum value. Preferably, the currents to each measurement electrode are respectively increased and decreased in the same time period, or substantially simultaneously. Preferably, reducing and supplying the current in the step follows the same constraints preferred above.

Another step of various embodiments of the present invention includes repeating one, all, or some combination of the above steps substantially continuously during the subject or patient measurement period. This repetition allows the various embodiments of the present invention to monitor the impedance of the electrodes in an essentially continuous manner. Monitoring the impedance includes the measurement of electrode voltage and calculation of the impedance value for a given electrode. By substantially continuously, it is meant that the system is measuring the impedance of at least one electrode preferably every 5 minutes, more preferably every 4 minutes, yet more preferably every 3 minutes, still more preferably every 2 minutes, even more preferably every 60 seconds, and most preferably less than 60 seconds.

Monitoring the electrodes in a continuous fashion preferably is only limited by the length of time during which the electrical current is progressively increased or decreased. The impedance calculation, as described above, relies on a known current value and the resultant measured voltage. When the current is progressively changing, it is not a known value and therefore the voltage is much more difficult to measure accurately and impedance is more difficult to calculate. Therefore, as the progressive increase or decrease of the current preferably requires at least 0.25 second, there is a minimum delay of 0.25 second between impedance measurements for any two electrodes. Preferably also, the impedance is not measured during those periods of time when the current being increased and decreased.

The actual time required to measure the voltage after the current being supplied reaches the maximum current needed to check for impedance is at least 1 cycle of the supplied current. Therefore frequency of the supplied current affect the measurement time. At lower frequencies such as 1 Hz—the measurement time is at least 1 second. If the electrical current is supplied at a high frequency, such as greater than the upper limit of the bio-band of the given physiological signal (e.g. 165 Hz for EEG monitoring which has an upper bio-band limit of 120 Hz), then there is substantially no delay from the signal itself. Therefore, the impedance measurement period must be at least one cycle of the given current frequency. If the current is supplied at 60 Hz, then the measurement must be taken for at least 1/60 second. The higher the frequency chosen, the shorter the measurement time period can be, though the measurement can be taken for longer than one cycle. Extending the measurement period may create a delay between impedance measurements of electrodes.

Now referring to the FIGS. 1-9, FIG. 1 is a block diagram of a system for monitoring and real-time therapy applications, and in this particular embodiment a seizure detector. The system can be connected to the subject or patient either on the subject or patient's scalp 19 with mounted surface electrodes 1, intra-cranial cortical grids 2, or implanted deep brain electrode(s) 3. The electrode leads 1b are preferably connected to the system via a yoke 4 containing cardiac defibrillation resistors (not shown) designed to absorb the energy of a cardiac defibrillation pulse. These resistors (not shown) and the associated electronics in the front-end of the instrumentation amplifiers (not shown) are designed to protect the instrumentation electronics and in particular applications to have electromagnetic interference filters (EMF) to eliminate interference caused by other electrical devices, while still ensuring that most of the energy delivered by the pulse is used for the intended therapy. The brainwave signals are then amplified and digitized by an analog-digital converter (ADC) circuitry 5.

In addition, a signal quality (SQ) circuitry 6, 7 can be used to provide measurement currents to the leads in order to calibrate the instrumentation amplifiers and measure electrode impedance. Similar SQ circuitry monitors the front-end amplifiers in order to detect eventual saturation that occurs when leads 1b are disconnected. This information, along with the digitized brainwave signals, is relayed to the processor 8-14, which contains the electrode impedance measurement module 8a. The electrode impedance module is the portion of the processor which embodies the present invention and thus provides an electrical current to the electrodes as described above, and measures the resultant electrical impedance to determine the quality of the signal being supplied through each electrode.

The processor (not shown) is composed of the subsystems 8 thru 14. The signal quality assessment module 8 is used to check whether each signal acquired by the system is of sufficient enough quality to be used in the subsequent analysis. The present invention 8a, in its various embodiments, lies, in part, within the signal quality assessment module 8. The present invention also, in part, is one portion of the process for determining the quality of the signal, that being in accurately determining the electrical impedance in physiological electrodes, without substantially limiting the ability to continue to collect physiological signals from the electrodes. Generally, signal quality assessment is carried out by two main steps: first, by removing noise from interference, and also by substantially continuously measuring the electrode impedance of each brainwave channel. In particular, one key area for noise in signal quality is in the 50 to 60 Hz range produced by a poor electroo-magnetic environment about the electrodes or the device. At high levels of 50 or 60 Hz indicate either a poor electromagnetic environment, or a poor connection to the subject or patient which will result in a heightened sensitivity of the system for any other environmental noise (e.g., lead movement, vibration, etc.). High levels of 50 or 60 Hz noise are usually indicative of poor signal quality. If signal quality is low (regarding the present invention, the electrical impedance of electrode[s] is too high), the user has several options. Electrodes can be replaced, conductive gel can be reapplied, or the electrode can be slightly moved and/or the skin re-abraded to renew the signal quality.

The present invention 8a focuses, in part, on the measurement of individual electrode impedance for ensuring signal quality. If electrode impedance is too high, then the signal being monitored faces heightened resistance and often is corrupted by further noise or artifacts created due to this increased resistance. To perform the impedance measurement, a current is supplied to each measurement electrode, either individually or simultaneously, at a known amplitude and frequency. The voltage across the given measurement electrode(s) and the reference electrode that is created due to this current is then measured by the system. The measured voltage and the known current are then used to calculate the impedance value of the given electrode(s). FIGS. 2-9 show different embodiments for conducting this impedance measurement, preferably substantially continuously.

If the signal quality and electrode impedance are good, the system preferably proceeds by analyzing the acquired signals in order to detect the presence of environmental or physiological artifacts, which may be corrupting the signal. This analysis is done in the artifact identification and measures computation module 9. With the methods or algorithms of the present invention several artifact detection methods or algorithms are used in combination. These artifact detection methods or algorithms analyze the signal for artifacts using combinations of both sensitivity specific and specificity specific methods or algorithms, each detecting the presence of artifacts in different ways, and those measures are combined to increase the accuracy of artifact detection in the combination and decision module 10. These techniques are described in greater detail in FIGS. 3 and 4. In addition methods or algorithms used in these combinations are further described in FIGS. 7-10. Other artifact detection techniques may be used as well in the system, devices or methods of the present invention. Some artifacts, such as ocular artifacts, can be removed from the signal by using a de-noising method. This is done at the level of the artifact detection & removal module 11.

De-noised and artifact-free signals are sent to the brain-wave analysis/processing module 12. This sub-system derives information contained in the signal, such as the level of consciousness or cortical quantification of the subject or patient, the presence of electro-cortical silence and abnormal brain/cortical activity such as seizure, ischemia, aneurysm, etc. This information can be used to identify one ore more brain/cortical abnormalities as well as quantifying brain/cortical activity in general for the subject or patient.

The automated detection & decision module 13 is where the processed signal is analyzed to determine the presence of any brain/cortical activity abnormalities that may be present. It uses a method that amplifies abnormal spike activity in the signal, while minimizing the background 'normal' brain activity. It also combines the real-time seizure index with the information obtained in the brainwave analysis/processing module 12 in order to provide an accurate diagnostic of the subject or patient's brain state.

A user interface module 14 provides the means for the user to interact with the system. In the preferred embodiment, this is done through the use of a display 16, which can be a touch screen display. The display 16 is used to warn the user, in real-time, of the presence of seizures. In addition, the user interface module 14 archives all the acquired signals and processed variables into a mass storage device 15, for later review.

The mass storage device 15 is used as a long term storage archive for all of the acquired EEG signals as well as the accompanying processing results. These data will then be available for later use. The signals will then be available for historical use and review where clinicians or researchers can check for artifacts or other abnormal brain activity; for example, seizures and the like. A raw EEG signal or an artifact free EEG signal can be stored in the mass storage device 15 or a corrupted signal can be stored as well with the artifacts identified as part of the signal. Furthermore, they can be used as a database from which signals can be used for baseline determination or calibration of artifact detection techniques.

Finally, in some embodiments, the system is connected to a mechanism that automatically delivers a treatment to the subject or patient, referred in the schematic as the treatment delivery device 18. The output of the system through a processor (not shown) can be used with the treatment delivery device including a processor in closed loop 17, partially closed loop or open loop to automatically deliver physical, electrical or chemical treatment to the subject or patient automatically based on the occurrence of abnormal brain activity, and monitor the effectiveness of such treatment in real time.

Figure 2:
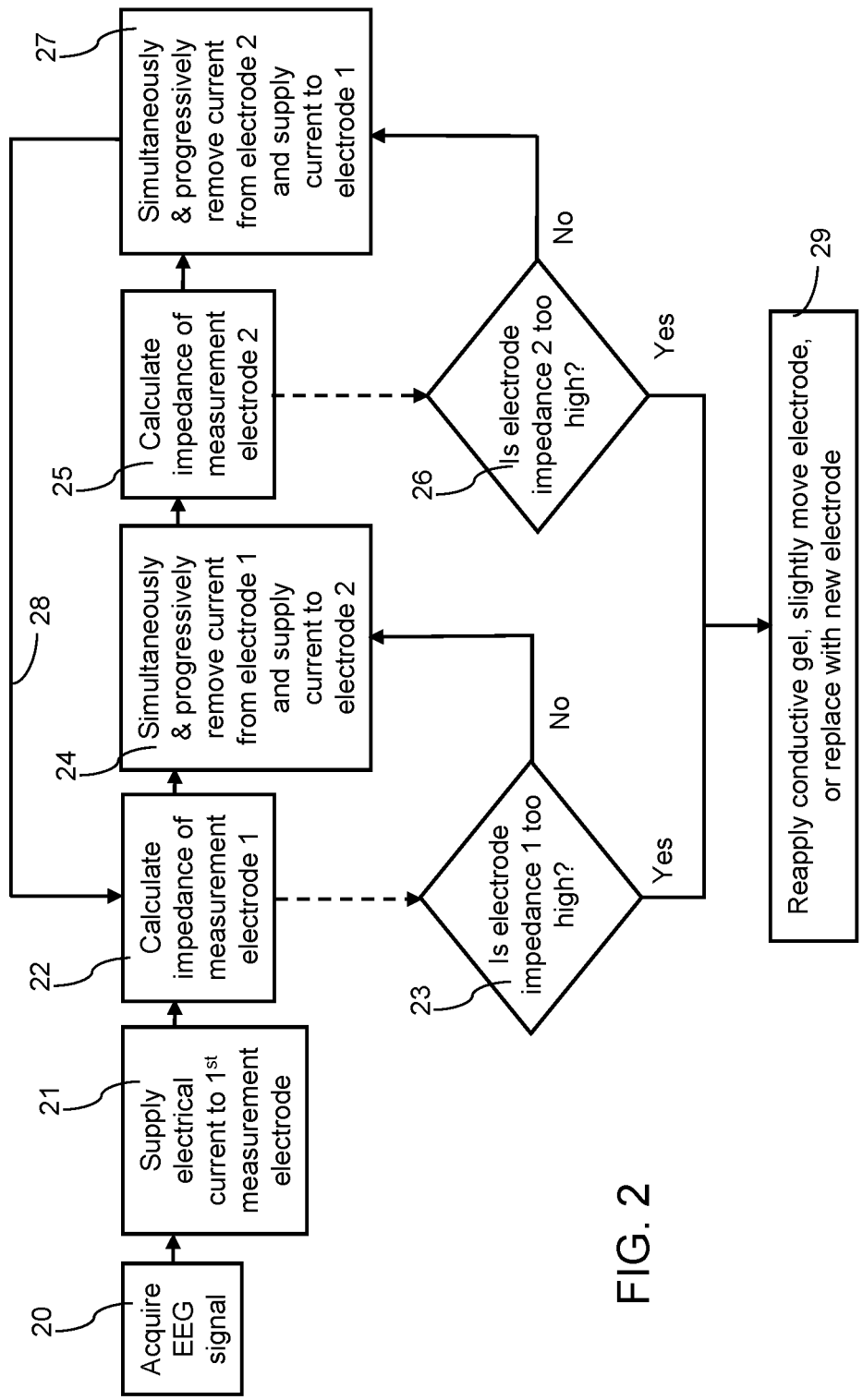
FIG. 2. Flow diagram depicting one embodiment of electrode impedance measurement and decision methods based on impedance measurements.

FIG. 2 is a flow diagram showing one embodiment of the present invention's electrode impedance measurement that involves measuring the impedance of each physiological electrode individually. An EEG signal 20, or other physiological signal, is acquired through the appropriate circuitry and begins to be displayed through a processor (not shown) on to a monitor (not shown). An electrical current is supplied to the first measurement electrode 21. This initial electrical current can be supplied substantially instantaneously or progressively by slowly increasing the level of the current over time until the predetermined level is reached. Preferably, the current is supplied progressively, starting at zero µA and increasing to the predetermined level over a period of time not less than 0.25 seconds and not more than 5 minutes, in order to minimize or even eliminate perturbation in the EEG or other physiological signal being measured.

Once the electrical current being supplied to the first measurement electrode has reached the predetermined maximum stabilized current, the voltage resulting from the supplied current is measured across the system (not shown). The voltage and current values are known to the system and are used to calculate an electrical impedance of the first measurement electrode 22. Preferably, this voltage measurement and impedance calculation is carried out over a period of time of one cycle depending on the frequency (not shown). The resultant impedance value calculated for the first measurement electrode is compared 23 against a threshold value to determine whether the electrode is providing as clear a signal as possible for accurate EEG or other physiological signal display. This threshold value is determined by the application as to the sensitivity necessary to provide a good physiological signal. If the electrical impedance calculated in the first measurement electrode is too high, then a technician or operator is notified (not shown) and he or she decides what type of action is required to renew the quality of the signal 29.

However, if the electrical impedance calculated in the first measurement electrode is at an acceptable level and the electrode is therefore producing a good quality signal, the system moves on to measure the electrical impedance in the subsequent electrode(s). In order to measure the next electrode, the electrical current is progressively removed from the first measurement electrode while an electrical current is supplied to the second measurement electrode 24. Preferably, the current to the first measurement electrode is removed simultaneously with supplying the current to the second measurement electrode. More preferably, the currents are removed and supplied in substantially the same time period. Whereas the initial electrical current above could be supplied either substantially instantaneously or progressively, all currents thereafter must be supplied and/or removed progressively. Here, the electrical current that was being supplied to the first measurement electrode is progressively removed by gradually decreasing the level of the electrical current from the predetermined measurement value down to a value of zero over a period of time not less than 0.25 seconds and not more than 5 minutes. Simultaneously, an electrical current is supplied to the second measurement electrode progressively starting at a value of zero and increasing the level of the electrical current over the same period of time, not less than 0.25 seconds and not more than 5 minutes, until the current reaches the predetermined value for measurement (not shown).

Once the electrical current being supplied to the first measurement electrode has been completely removed and the electrical current being supplied to the second measurement electrode has reached the predetermined level for measurement, the voltage resulting from the supplied current is measured across the system (not shown). The voltage and current values are known to the system and are used to calculate an electrical impedance of the second measurement electrode 25. Preferably, this voltage measurement and impedance calculation is carried out over a period of time of not less than 1 second. The resultant impedance value calculated for the second measurement electrode is compared 26 against a threshold value to determine whether the electrode is providing as clear a signal as possible for accurate EEG or other physiological signal display. If the electrical impedance calculated in the second measurement electrode is too high, then a technician or operator is notified (not shown) and he or she decides what type of action is required to renew the quality of the signal 29.

Similar to above, if the electrical impedance calculated in the second measurement electrode is at an acceptable level and the electrode is therefore producing a good quality signal, the system either moves on to the next subsequent electrode to be measured (if the particular embodiment includes three or more measurement electrodes) (not shown) or returns back to the first measurement electrode to repeat the process. In the case of a system with two measurement electrodes, the current being supplied to the second measurement electrode is progressively removed over a period of time not less than 0.25 seconds and not more than 5 minutes, while an electrical current is simultaneously supplied back to the first measurement electrode over the same time period 27. The system then loops back 28 to repeat the process continuously as long as necessary.

Figure 3:
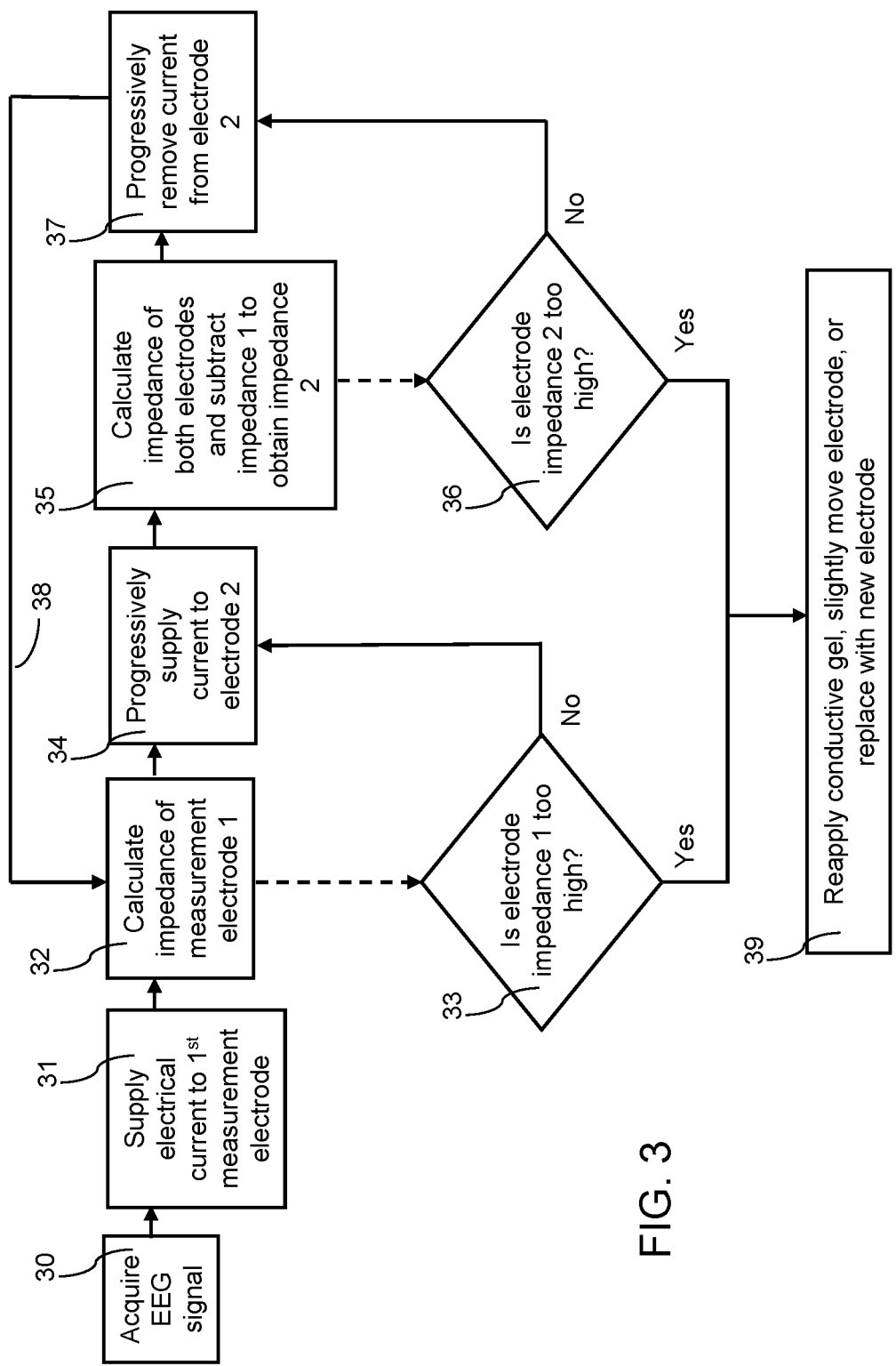
FIG. 3. Flow diagram depicting another embodiment of electrode impedance measurement and decision methods based on impedance measurements.

FIG. 3 is a flow diagram showing another embodiment of the present invention's electrode impedance measurement that involves alternating the measurement of electrode impedance between one electrode individually and then a combination of that same reference electrode along with each measurement electrode. An EEG signal 30, or other physiological signal, is acquired through the appropriate circuitry and begins to be displayed through a processor (not shown) on to a monitor (not shown). An electrical current is supplied to the reference electrode 31. This initial electrical current can be supplied substantially instantaneously or progressively by slowly increasing the level of the current over time until the predetermined level is reached. Preferably, the current is supplied progressively, starting at zero µA and increasing to the predetermined level over a period of time not less than 0.25 seconds and not more than 5 minutes, in order to minimize or even eliminate perturbation in the EEG or other physiological signal being measured.

Once the electrical current being supplied to the first measurement electrode has reached the predetermined level, the voltage resulting from the supplied current is measured across the system (not shown). The voltage and current values are known to the system and are used to calculate an electrical impedance of the first measurement electrode 32. Preferably, this voltage measurement and impedance calculation is carried out over a period of time of not less than 1 cycle of the supplied current (not shown). The resultant impedance value calculated for the reference electrode is compared 33 against a threshold value to determine whether the electrode is providing as clear a signal as possible for accurate EEG or other physiological signal display. If the electrical impedance calculated in the reference electrode is too high, then a technician or operator is notified (not shown) and he or she decides what type of action is required to renew the quality of the signal 39.

However, if the electrical impedance calculated in the first measurement electrode is at an acceptable level and the electrode is therefore producing a good quality signal, the system moves on to measure the electrical impedance in the subsequent electrode(s). In order to measure the next electrode, the electrical current being supplied to the first measurement electrode is maintained while an electrical current is progressively supplied to the second measurement electrode 34. Whereas the initial electrical current above could be supplied either substantially instantaneously or progressively, all currents thereafter must be supplied and/or removed progressively. Here, the electrical current supplied to the first measurement electrode is maintained substantially unchanged while simultaneously, an electrical current is supplied to the second measurement electrode progressively starting at a value of zero and increasing the level of the electrical current over a period of time not less than 0.25 seconds and not more than 5 minutes, until the current reaches the predetermined value for measurement (not shown).

Once the electrical current being supplied to the second measurement electrode has reached the predetermined level for measurement (the same level as the current supplied to the reference electrode), the voltage resulting from the supplied current is measured across the system (not shown). The voltage and current values are known to the system and are used to calculate an electrical impedance of the second measurement electrode 35. Preferably, this voltage measurement and impedance calculation is carried out over a period of time of not less than 1 cycle of the supplied current. The resultant impedance value calculated for the combination of the first and second measurement electrodes is compared 36 against a threshold value to determine whether the combined impedance measurement is indicative of one of the electrodes either failing or providing as clear a signal as possible for accurate EEG or other physiological signal display. If the combined electrical impedance calculated for the reference electrode and first measurement electrode is too high, then a technician or operator is notified (not shown) and they decide what type of action is required to renew the quality of the signal 39.

Similar to above, if calculated electrical impedance for the combination of the first and second measurement electrodes is at an acceptable level and the electrode is therefore transmitting/providing a good quality signal, the system progressively removes the electrical current 37 being supplied to the second measurement electrode by gradually removing the electrical current over a period of time not less than 0.25 seconds and not more than 5 minutes and loops back 38 to repeat the measurement process for the reference electrode alone. The above steps are then repeated for the second measurement electrode (not shown) and any subsequent measurement electrodes (not shown), each time alternating the measurement of impedance between measuring the first measurement electrode alone followed by a measurement of the first measurement electrode combined with a subsequent measurement electrode (not shown). The system then loops back 28 to repeat the process continuously as long as necessary.

Figure 4:
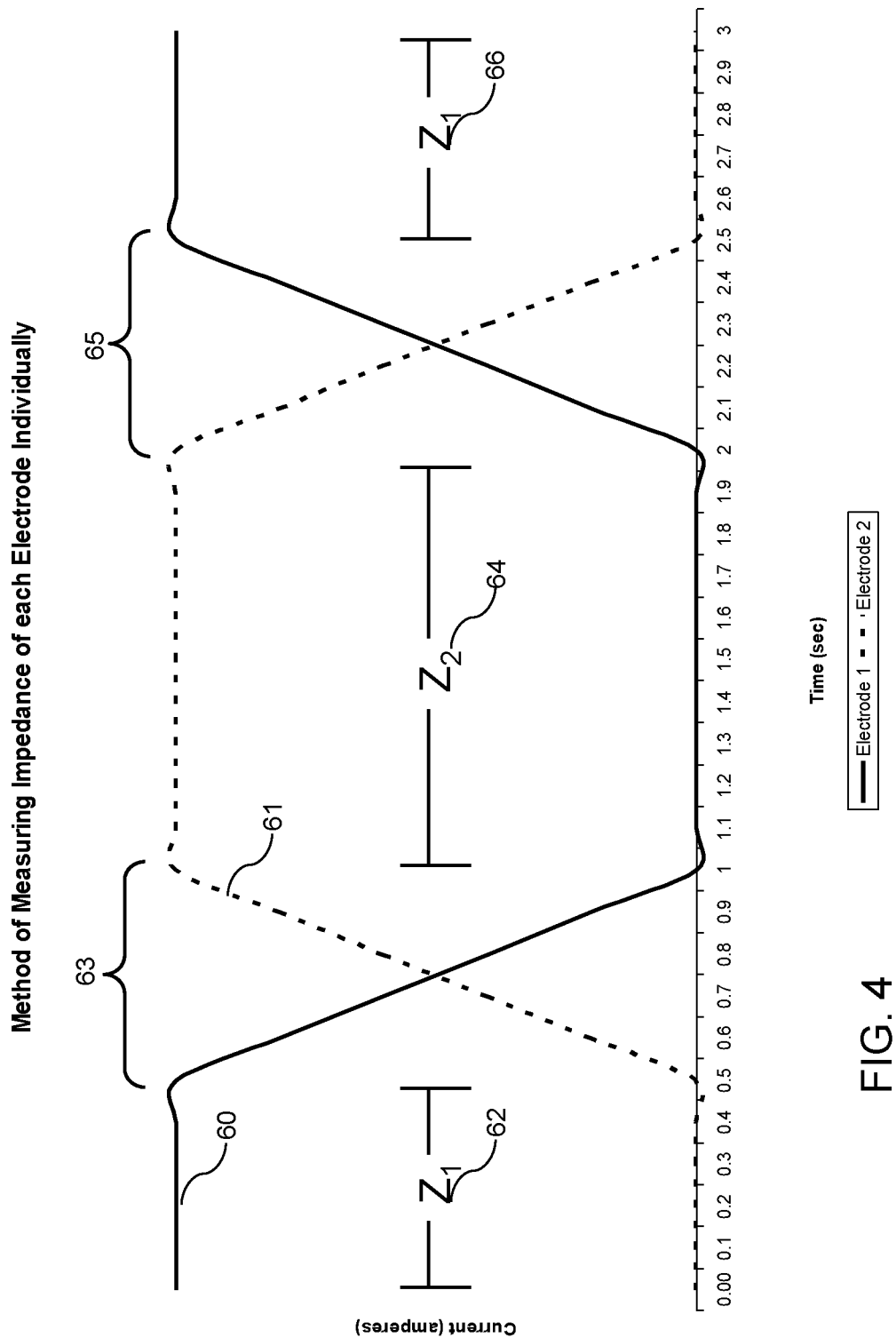
FIG. 4. Graphical representation of electrical currents used for the embodiment of one method of calculating impedance of electrodes by measuring each electrode individually.

FIG. 4 is a graphical representation of one embodiment of the electrical currents utilized within the present invention's impedance measurement process. This is also another method of depicting the method described in FIG. 2. This method involves calculating the electrical impedance of each measurement electrode individually and alternating between each measurement electrode in turn. An electrical current is supplied to the first measurement electrode 60 and the resulting voltage (not shown) is measured across the electrodes and used to calculate electrical impedance 62 in the first measurement electrode. The next time period 63 is when the electrical current is progressively removed from the first measurement electrode and simultaneously progressively supplied to the second measurement electrode. Once the electrical current supplied to the second measurement electrode 61 reaches the predetermined level and the current has been completely removed from the first measurement electrode, electrical impedance of the second measurement electrode 64 is calculated using the electrical current supplied and the voltage measured across the electrodes. After the measurement time period for the second measurement electrode, the currents are alternated again over a time period 65 of progressive electrical current removal and addition similar to above. The process is then repeated for the first measurement electrode to calculate impedance for that electrode 66.

Figure 5:
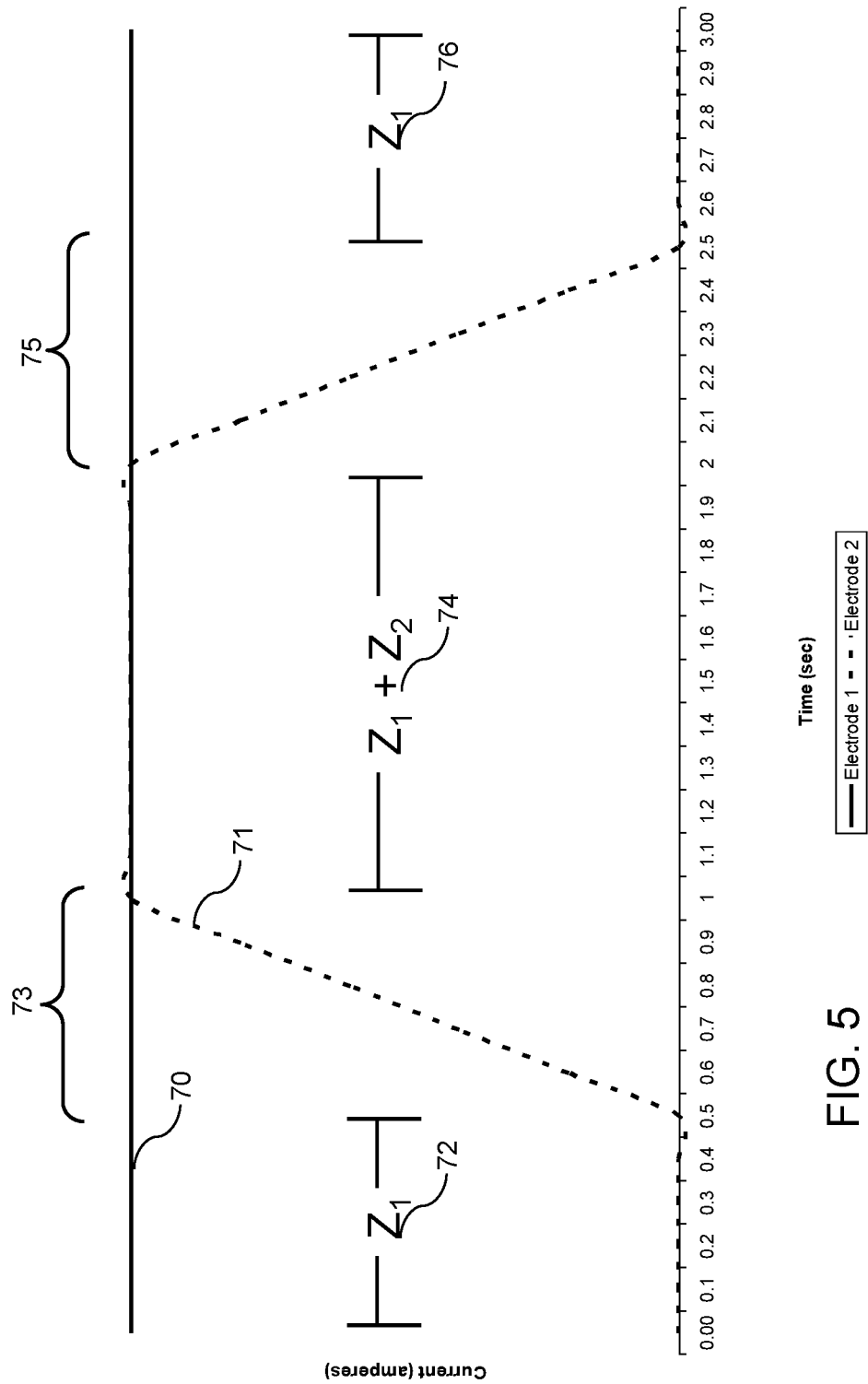
FIG. 5. Graphical representation of electrical currents used for the embodiment of one method of calculating impedance of electrodes by alternating between measuring one electrode individually and multiple electrodes simultaneously.

FIG. 5 is a graphical representation of another embodiment of the electrical currents utilized within the present invention's impedance measurement process. This is also another method of depicting the method described in FIG. 3. This method involves calculating the electrical impedance of a reference electrode individually and then the electrical impedance of a combination of the reference electrode and each measurement electrode in turn. An electrical current is supplied to the first measurement electrode 70 and the resulting voltage (not shown) is measured across the electrodes and used to calculate electrical impedance 72 in the first measurement electrode. The next time period 73 is when an electrical current is progressively supplied to the first measurement electrode while the electrical current supplied to the reference electrode is held substantially constant. Once the electrical current supplied to the first measurement electrode 71 reaches the predetermined level, electrical impedance of the reference electrode and first measurement electrode combined 74 is calculated using the electrical current supplied and the voltage measured across the electrodes. After the measurement time period for the combination of reference and first measurement electrodes, the current is progressively removed over a time period 75 of progressive electrical current removal and addition similar to above. The process is then repeated for the first measurement electrode to calculate impedance for that electrode 76.

Figure 6A:
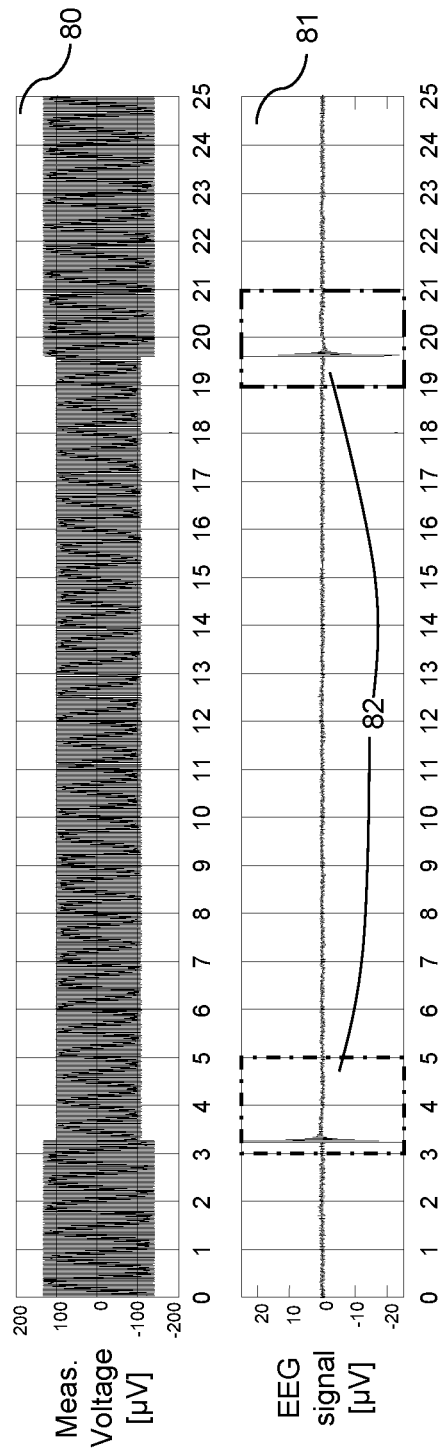
FIGS. 6A-B. Graphical representation of the relationship between the measured voltage across physiological electrodes (EEG) and the resulting EEG waveform due to two methods of altering the electrical current supplied for impedance measurement.
Figure 6B:
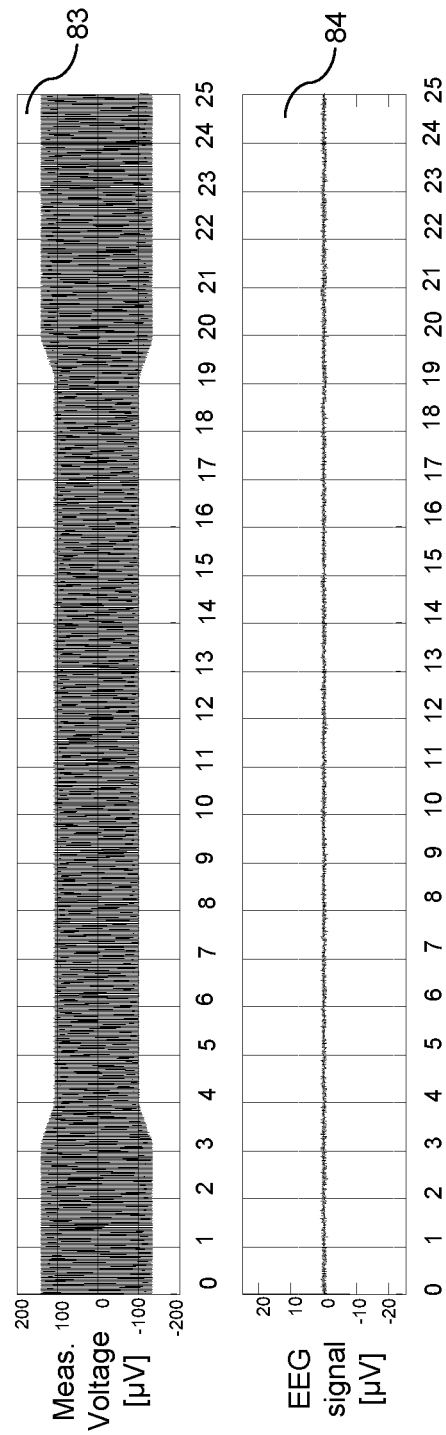

FIGS. 6A-B are a graphical representation of the effect on an EEG signal resulting from the addition or removal of an electrical current from an electrode. The measured voltage is a direct product of the electrical current supplied to the electrode. FIG. 6A shows that when the current is supplied or removed substantially instantaneously (the level of the electrical current increasing from zero to the predetermined measurement value in not less than 0.25 seconds, or vice versa) 80, the resulting EEG signal 81 experiences a large perturbation 82 that decreases the usefulness of that particular portion of the EEG signal. The lined box portion 82 of the EEG signal 81 represents the entire portion of the EEG epoch that would likely need to be discarded as a result of the perturbation caused by the sudden increase or decrease in the electrical current and resulting measured voltage.

However, FIG. 6B shows that if the electrical current is supplied and removed progressively, over a period of time 83, the resulting EEG signal 84 displays no perturbation. This lack or perturbation means that no portion of the recorded EEG signal needs to be discarded and the entire signal can be used for accurate analysis of the subject or patient's brain activity. Although the figure portrays an EEG signal, similar results would arise through utilization of this method in virtually any physiological signal.

Figure 7B:
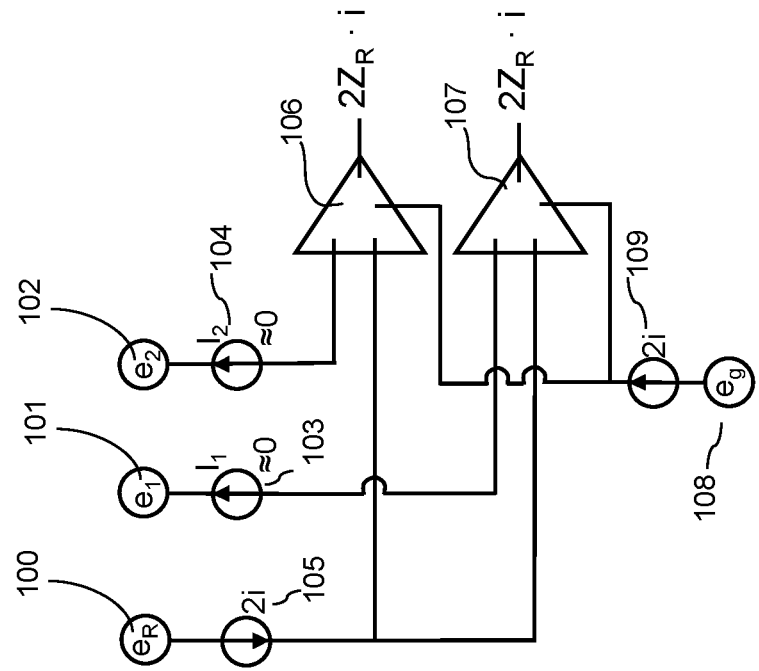
FIGS. 7A-B. Diagram depicting an example of a multiple lead referential system of measurement of electrical impedance in physiological electrodes.
Figure 7A:
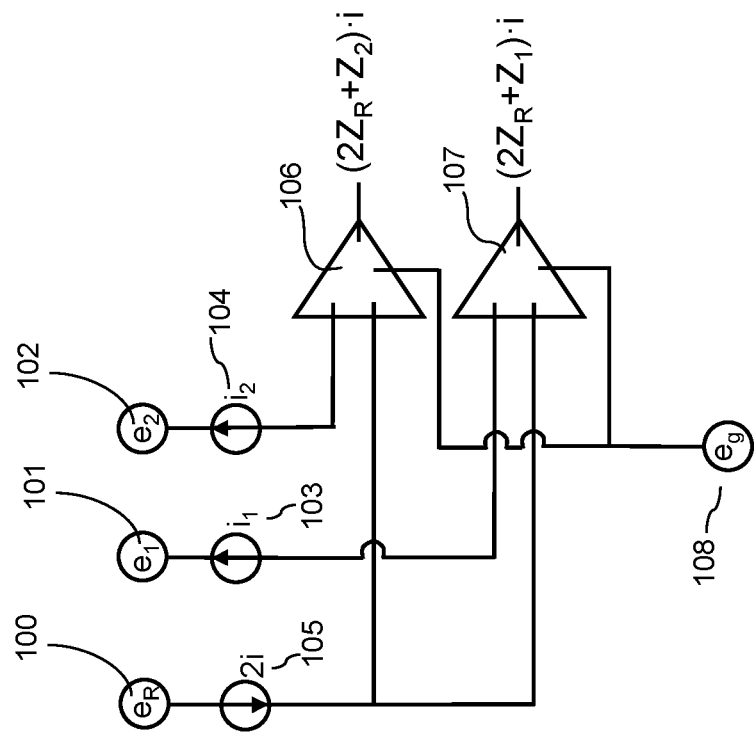

FIGS. 7A-B are an electrical schematic of one embodiment of the present invention utilizing four electrode leads in a referential system; where each electrode is compared against a reference electrode 100 as described above. The reference electrode 100 is connected to the subject or patient (not shown) in conjunction with two measurement electrodes 101-102. Also included is a grounding electrode 108.

In order to calculate the electrical impedance of the individual measurement electrodes 101, 102, the first step as depicted in FIG. 7A, consists of supplying electrical currents 103, 104 at a known amplitude and frequency to each measurement electrode individually. The currents 103, 104 supplied to the two measurement electrodes 101, 102 is pulled from the reference electrode 100, which is equivalent to having another current source 105 at the same frequency (albeit twice the amplitude and in phase opposition) in the reference electrode lead. The voltages being measured (not shown) across each measurement electrode 101, 102 and the reference electrode 100 by the differential amplifiers 106, 107 are thus proportional to the sum of twice the reference electrode impedance and the corresponding measurement electrode impedance.

Once this first impedance measurement is made, the second step, as depicted in FIG. 7B, consists of progressively decreasing the amplitude of the current sources 103, 104 to a value substantially equal to zero (0), as described above. To respect Kirchhoff's circuit law (which states the sum of currents provided to a circuit is always 0), the current drawn from the reference electrode returns to the amplification circuitry through the ground electrode 108. This is equivalent to having a current source 109 in the ground lead equal in amplitude and frequency to the current source 105 of the reference lead, but in phase opposition. In this case, the voltages measured by the two differential amplifiers 106, 107 are proportional to the current source amplitude and the reference electrode impedance.

Using the measurement derived from each circuit configuration (FIGS. 7A and 7B), and knowing the amplitude of the current source, one can easily derive each electrode impedance. To allow for continuous operation, once the second measurement is performed (FIG. 7B), the system just needs to progressively increase the amplitude of the two current sources 103, 104 to return to the first configuration.

Another embodiment of this circuitry and method is presented in FIGS. 8A-B. In this embodiment, we assume that we have a referential system with N channels, one reference electrode 110, N measurement electrodes 111, 112, 113 and one ground electrode 120. We further assume for simplicity that N is an even number.

In the first configuration, depicted in FIG. 8A, the circuit has N active current sources 114, 115, 116 at the same amplitude and same frequency. We alternate the polarity of these current source is such a way that the sum of all current delivered to the measurement electrodes is zero (0) (if we did not alternate the current sources, the current returning through the ground electrode 120 would be equal to the sum of all currents, which may violate the leakage current requirements for medical device, in particular if the number of channels is large). For instance, as represented in FIG. 8A, the current is positive going to each even-numbered measurement electrode 112, and negative going to each odd-numbered measurement electrodes 111, 113. The voltages measured by the differential amplifiers 117, 118, 119 are thus proportional to the current amplitude and each measurement electrode.

In the second configuration, as depicted in FIG. 8B, we progressively increase the current source 121 in the reference electrode. In this embodiment, and for simplicity, this current source 121 has the same frequency and amplitude as the current sources 114, 115, 116 in the measurement electrode leads. The current 121 drawn from the reference electrode returns from the ground electrode 120. In this configuration, the voltages measured by the differential amplifiers 117, 118, 119 are proportional to the sum of the reference and each measurement electrode impedance. Using the measurement obtained in the first configuration (FIG. 8A), the reference electrode impedance measure can be easily derived. To continuously measure the electrode impedance, one would alternate between each configuration (FIGS. 8A and 8B) and progressively decreasing or increasing the current source in the reference electrode lead.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claims:

1. A device for a simultaneous measurement of physiological signals, and a measured and calculated electrical impedance of applied physiological electrodes comprising:
   at least three electrodes adapted to be attached to and/or embedded into a subject, at least one electrode being for electrical grounding, at least one electrode providing a reference signal, and at least one physiological measurement electrode for acquisition of a physiological signal;
   a processor adapted for collection of the physiological signal and determining the calculated electrical impedance of each electrode individually;
   a variable current source capable of progressively increasing and decreasing electrical current into the individual electrodes steadily over a period of time for impedance measurement of the electrodes; and
   a monitor adapted to display the physiological signal and the calculated electrical impedance for each electrode utilized.

2. The device of claim 1 where the variable current source provides an electrical current at a frequency between 52 Hz and 58 Hz, exclusive.

3. The device of claim 1 wherein the variable current source is adapted to progressively increase and decrease the electrical current in order to eliminate perturbation of the physiological signal from supplying the electrical current.

4. The device of claim 1 where the variable current source provides a current waveform containing a number of frequencies that are outside a bioband of the physiological signal, where the bioband is comprised of all frequencies that carry any information used for diagnostic, prognostic, triage, or treatment purposes, and the maximum level of the impedance measurement current supplied is less than 5 µA.

5. The device of claim 1 wherein the physiological measurement electrode is an ECG electrode.

6. The device of claim 1 wherein the physiological measurement electrode is an EOG electrode.

7. A system for the simultaneous measurement of physiological signals and electrical impedance of applied physiological electrodes comprising:
   at least three electrodes adapted to be attached to a subject, at least one electrode being for electrical grounding, at least one electrode providing a reference signal, and at least one physiological measurement electrode for acquisition of a physiological signal;
   a processor adapted for collection of the physiological signal and determining the electrical impedance of each electrode individually;
   a variable current source capable of progressively increasing and decreasing electrical current into the individual electrodes steadily over a period of time for impedance measurement of the electrodes;
   the processor or a second processor adapted with brainwave analysis module for analyzing the physiological signal; and
   a monitor adapted to display the physiological signal, a brainwave analysis and/or a calculated electrical impedance for each electrode utilized.

8. The system of claim 7, wherein the brainwave analysis is a determination of a presence of any brain/cortical abnormalities that may be present in the subject.

9. The system of claim 8, wherein the brainwave analysis is adapted to amplify spike activity in the physiological signal while minimizing normal background brain activity.

10. The system of claim 7, wherein the brainwave analysis is adapted to provide an accurate diagnostic of the subject's brain state.

11. The system of claim 7, wherein the brainwave analysis is adapted to provide a level of consciousness or cortical quantification of the subject.

12. The system of claim 7, further including a treatment delivery device.

13. The system of claim 12 wherein the treatment delivery device delivers an electrical treatment to the subject based on the processed physiological signal.

14. The system of claim 12 wherein the treatment delivery device delivers a chemical treatment to the subject based on the processed physiological signal.

15. The system of claim 12 wherein the treatment delivery device is controlled in closed or partially open loop by the processor, the second processor, or a third processor based in part on the processed physiological signal.

16. The system of claim 7 where the variable current source provides an electrical current at a frequency between 52 Hz and 58 Hz, exclusive.

17. The system of claim 7 wherein the variable current source is adapted to progressively increase and decrease the electrical current in order to eliminate perturbation of the physiological signal from supplying the electrical current.

18. The system of claim 7 where the variable current source provides a current waveform containing a number of frequencies that are outside a bioband of the physiological signal, where the bioband is comprised of all frequencies that carry any information used for diagnostic, prognostic, triage, or treatment purposes, and the maximum level of the impedance measurement current supplied is less than 5 µA.

* * * * *